United States Patent [19]

Ludwigson

[11] 4,099,408
[45] Jul. 11, 1978

[54] METHOD FOR TESTING SHEET METALS

[75] Inventor: David C. Ludwigson, Hempfield Township, Westmoreland County, Pa.

[73] Assignee: United States Steel Corporation, Pittsburgh, Pa.

[21] Appl. No.: 812,974

[22] Filed: Jul. 5, 1977

[51] Int. Cl.$^2$ .............................................. G01N 3/08
[52] U.S. Cl. ...................................................... 73/95
[58] Field of Search .................................. 73/95, 88 R

[56] References Cited
U.S. PATENT DOCUMENTS

| | | |
|---|---|---|
| 3,733,049 | 5/1973 | Van den Hove et al. ........... 73/88 R |
| 3,927,558 | 12/1975 | Philippe et al. ........................... 73/95 |

Primary Examiner—Anthony V. Ciarlante
Attorney, Agent, or Firm—Rea C. Helm

[57] ABSTRACT

A method of determining properties of sheet metal uses a specimen having a full width section and a reduced width section about 95% the width of the full width section in a tensile test. The strain hardening exponent is calculated from thickness and width measurements made before and after the specimen is strained to failure. The same and other measurements are used to calculate yield strength, elongation, ultimate strength and plastic strain ratio. Particularly useful for continuously yielding materials, the yield strength may also be determined from calculations using the strain hardening exponent and the ultimate strength.

16 Claims, 1 Drawing Figure

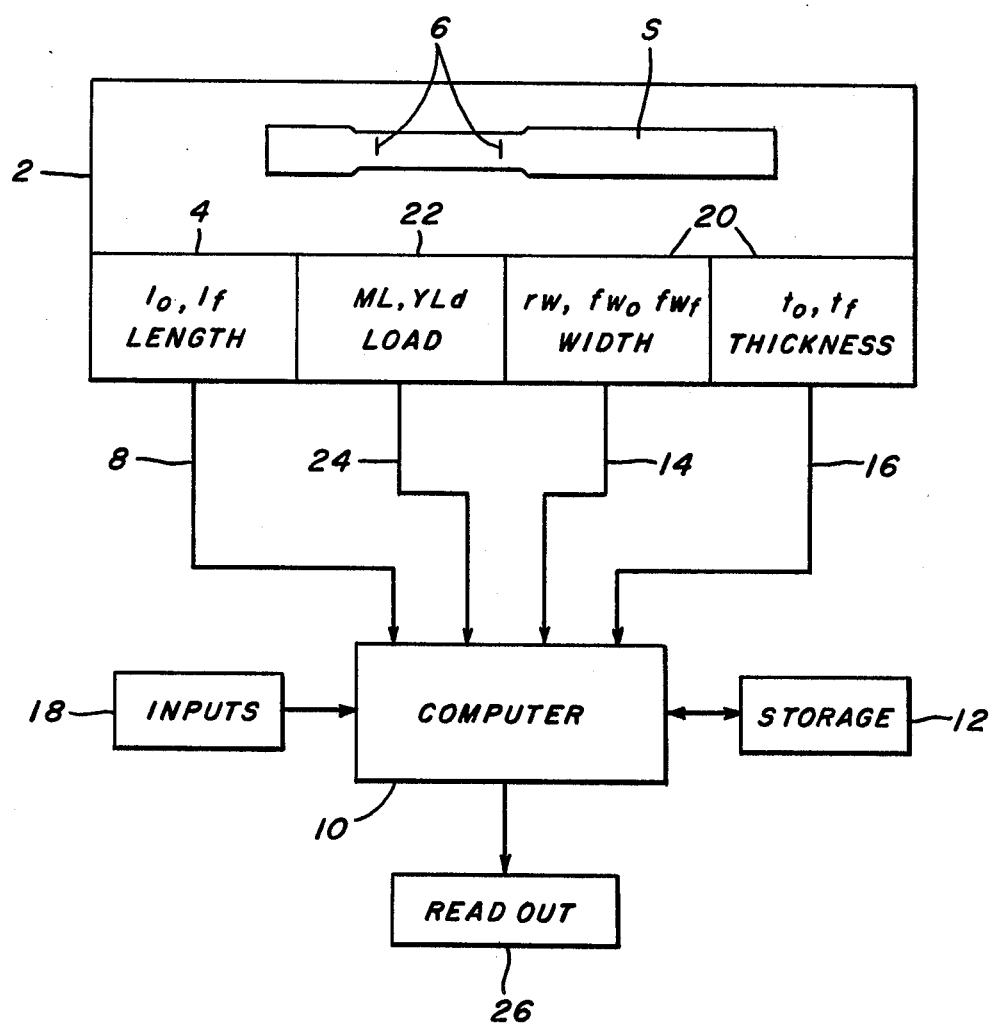

METHOD FOR TESTING SHEET METALS

FIELD OF THE INVENTION

This invention relates to a method for the testing of sheet metal and more particularly for determining the yield and ultimate tensile strength, elongation, the strain hardening exponent and the plastic strain ratio of a specimen of sheet steel.

BACKGROUND OF THE INVENTION

Determination of the formability properties of sheet steel is of great importance to both the manufacturers and users of sheet steels. One method of determining formability is the measurement of properties determined from tensile testing. The useful properties include the plastic-strain ratio, $r$, the ratio of width strain to thickness strain; the strain-hardening exponent, $n$, the slope of the true stress-true strain flow curve; elongation; yield strength and ultimate strength. There are many procedures in existence to measure these properties, but all methods that I am aware of are time consuming and costly and require exacting sample preparation and considerable testing skill. As a result, these methods have been largely limited to experimental work in the laboratory, and have had very limited use in the manufacturing plant or in the users shop.

SUMMARY OF THE INVENTION

In accordance with my method, a specimen of the sheet metal is punched out in a specimen press. The specimen has a reduced width section, $rw$, which is about 95% of the width of the full width, $fw_o$, section. Length measuring marks are placed on the reduced width section spaced apart a distance $l_o$. The thickness of the specimen, $t_o$, the widths of the reduced width section, $rw$, and the full width section, $fw_o$, and the length between marks, $l_o$, are measured and noted. The specimen is strained to failure noting the thickness $t_f$, and width $fw_f$ of the full width section, the distance $l_f$ between the marks, the maximum load, ML, and the discontinuous yield load, $YLd$, if yielding is discontinuous. If the yielding was discontinuous, the discontinuous yield strength, YSd is determined using the expression, $$YSD = (YLd)/(rw \cdot t_o) - 50{,}000 \cdot t_o \quad (1)$$

This is the conventional definition of yield strength except for the last term which is a correction for the influence of the sheared specimen edges when the cold-worked edges are not removed.

The ultimate tensile strength, UTS, is determined using the expression, $$UTS = (ML)/(rw \cdot t_o) - 50{,}000 \cdot t_o \quad (2)$$

This is the conventional definition of ultimate tensile strength, also corrected, however, for the influence of sheared edges.

Elongation, EL, is determined from the conventional definition using the expression, $$EL\% = [(l_f/l_o) - 1] \cdot 100\% \quad (3)$$

The plastic strain ratio, r, is determined by the expression, $$r = [\ln(fw_f/fw_o)]/[\ln(t_f/t_o)] \quad (4)$$

which is derived from the definition of r, the ratio of the true width strain to the true thickness strain.

The strain hardening exponent, $n$, is determined by calculations using a new method which may be determined as outlined below.

By definition, true strain, $\epsilon$, may be expressed as, $$\epsilon = \ln \frac{w_o \cdot t_o}{w_i \cdot t_i} \quad (5)$$

where $w$ and $t$ represent width and thickness and the subscripts o and i designate original and instantaneous values respectively. Since $\epsilon = n$ at the maximum load in a tensile test, equation 5 may be rewritten as, $$n = \ln \frac{w_o \cdot t_o}{w_i \cdot t_i} \quad (6)$$

By definition, true stress may be expressed as $K \cdot \epsilon^n$, where K is a strength factor and may also be expressed as $P/w_i t_i$, where P is the load. Combining these definitions with equation 5 and rearranging provides the expression, $$\frac{P}{K} = w_i t_i (\ln \frac{w_o \cdot t_o}{w_i \cdot t_i})^n \quad (7)$$

By applying the definition stated in equation 6 and applying the definition of logarithms to equation 6 and substituting, the right hand side of equation 7 becomes $w_o \cdot t_o \cdot n^n/e^n$, where e is the base of natural logarithms. If the reduced width portion of the sample, $rw$, is substituted for $w_o$, then equation 7 may be rewritten for the reduced width section at maximum load as, $$P/K = rw \cdot t_o \cdot n^n/e^n \quad (8)$$

By substituting notations for the full width in equation 7, the full width section in equation 7, at maximum load it becomes, $$\frac{P}{K} = fw_f \cdot t_f (\ln \frac{fw_o \cdot t_o}{fw_f \cdot t_f})^n \quad (9)$$

Because P/K is the same for both sections at full load, equations 8 and 9 may be combined into $$rw \cdot t_o \cdot \frac{n^n}{e^n} = fw_f \cdot t_f (\ln \frac{fw_o \cdot t_o}{fw_f \cdot t_f})^n \quad (10)$$

By taking logarithms and rearranging, equation (10) can be rewritten as $$n = \frac{\ln rw + \ln t_o - \ln fw_f - \ln t_f - n}{\ln[\frac{(\ln fw_o + \ln t_o - \ln fw_f - \ln t_f)}{n}]} \quad (11)$$

This equation indicates that the strain hardening exponent, $n$, may be determined from thickness and width measurements only.

Test operators occasionally encounter difficulty in discerning the yield load for specimens which do not exhibit well-defined yield points or when the yielding is continuous. Accordingly, an alternative method for determining yield strength is provided based on knowledge of the strain hardening exponent, $n$, and the ultimate strength UTS.

The definition of true stress, $P/w_f t_i$ may be combined with the definition of engineering strain, $E$, $(l_1-l_o)/l_o$ to provide an alternate expression for true stress, assuming a constant volume, of $$\sigma = (P/w_o \cdot t_o)(1+E) \qquad (12)$$

This equation may then be equated with the flow curve model expression for true stress, $K \cdot \epsilon^n$, to provide $$K \cdot \epsilon^n = (P/w_o t_o)(1+E) \qquad (13)$$

If equation (13) is now considered at maximum load where P is ML, the ultimate tensile strength is $ML/w_o \cdot t_o$, $n$ is $\epsilon$ and if the relationship between true strain and engineering strain is included, equation (13) may be rewritten as $$K = UTS \cdot e^n/n^n \qquad (14)$$

This expression enables an evaluation of the constant, K, from a knowledge of ultimate tensile strength, UTS, and the strain hardening exponent, $n$. True stress may then be determined for any value of true strain, and the flow curve model for true stress of $K \cdot \epsilon^n$ may be rewritten as $$\sigma = UTS(e \cdot \epsilon)^n/n^n \qquad (15)$$

One criteria commonly used in defining yield strength is the 0.2% offset yield strength. By substituting the values at 0.2% offset and from the definition of yield strength at 0.2% offset, equation (12) may be rewritten as $$\sigma_{.002} = YS_{.002}(1+E_{.002}) \qquad (16)$$

where the subscripts indicate the 0.2% offset value. Since the engineering strain at 0.2% offset is 0.002, YS.002 is approximately equal to $\sigma_{.002}$. Equation (15) may then be rewritten as $$YS_{.002} = UTS(e \cdot \epsilon_{.002})^n/n^n \qquad (17)$$

The term in the parentheses is a constant, and equation (17) may be rewritten in general terms as $$YS = UTS(C/n)^n \qquad (18)$$

If the constant is designated as $C_{.002}$ and from the definitions of yield strength and ultimate strength, equation (17) becomes $$P_{.002} = ML \cdot C_{.002}{}^n/n^n \qquad (19)$$

Equation 19 may be used to evaluate the constant $C_{.002}$ empirically from yield-load - maximum-load data and the value of $n$. Once evaluated, $C_{.002}$ can be used in conjunction with equation 18 and known values of ultimate strength and $n$ to calculate the value of yield strength.

DESCRIPTION OF THE DRAWING

In the accompanying drawing, the single FIGURE is a block diagram illustrating schematically apparatus for carrying out the method of my invention.

DETAILED DESCRIPTION

Referring now to the drawing, reference numeral 2 refers to a tensile testing machine in which a specimen S, is mounted for the tensile test. About half the length of the specimen has a reduced width section and the other half a full width section. The reduced width section should be wide enough to provide sufficient strain in the full width section so that the thickness and width changes in the full width section may be measured after the specimen is strained to failure. A reduced width section about 95% as wide as the full width section is preferred. If the reduced width is below about 92% of the full width, too little of the strain will be in the full width section and the sensitivity of measurements will be substantially reduced. If the width is as much as 98%, imprecision is more likely because results become dependent on the increasingly smaller difference in the widths of the two sections.

The specimen may be quickly and conveniently punched from a sample by a simple punch press. A satisfactory guide for a diemaker is to make the reduced width section 95% of the full width section within a tolerance of plus or minus ½ of 1%. The sheared edges will only effect determinations of yield strength and ultimate strength and accordingly these determinations must be corrected for sheared edge as compared to conventionally prepared specimens.

The initial length, $l_o$, in the reduced width section is established by a gage marker 4 placing marks 6 on the specimen while the length, $l_o$, is noted as one of the inputs 8 to a computer 10. The marks 6 may also be placed on the specimen as part of the punch press operation. An extensometer mounted on the tensile testing machine may also be used providing a direct coupling to the computer. The initial length measurement is then stored in a storage 12 since it is only used in the conventional determination of elongation at the end of the test.

The specimen dimensions of $rw$, $fw_o$ and $t_o$ are determined and noted as inputs 14 and 16 to the computer. When a punched specimen is used, it is obviously simple to enter predetermined values into the computer through inputs 18. These dimensions may be obtained by measuring modules 20 sensing the width and thickness using direct current linear variable displacement transducers, or the dimensions may be obtained by the use of a micrometer and entered into the computer and stored for use at the end of the test.

The specimen is then strained to failure. A load sensor 22 provides the load input 24 to the computer and a readout 26 indicates the load on the specimen during the test. If the yielding of the specimen is discontinuous, the discontinuous yield load, YLd is noted on the readout and stored. The maximum load, ML, is noted on the readout and stored. The readout may be digital panel meters, dial meters or any other convenient readout of the force from load sensor 22.

The final dimensions $l_f$, $fw_f$ and $t_f$ are measured and the values entered into the computer. The properties determined in equations 1, 2, 3 and 4 may now be readily determined by the computer and displayed in a suitable manner by readout 26. Equation 11 is a transcendental equation which converges in several iterations to a sufficiently precise value for $n$. Computer 10 may be a mini-computer or a programmable calculator capable of an iterative solution for equation 11. The value for $n$ may also be displayed by readout 26.

Since the plastic strain ratio, r, often varies with the test direction in the plane of the rolled material, additional tests may be made. Specimens are punched from the sample oriented at proper angles, tested and the computer programmed to calculate normal plastic anisotropy and planar plastic anisotropy. n values may also be determined in different directions.

Where the yield is continuous and therefore difficult to determine, such as freshly temper-rolled carbon-steel sheet, the alternative method of calculating yield strength from the ultimate strength may be used. The appropriate value of C must be entered into the computer. Separate values of C would be used for each yield strength criteria, for example 0.2% offset, 0.5% extension under load or 10% extension under load. From a series of tests of annealed low-carbon sheet steel, C has been determined as 0.017 at 0.2% offset yield strength and 0.0235 at 0.5% extension under load.

EXAMPLE 1

A specimen was punched out from a sample of drawing-quality semi-killed rolled sheet steel. The following dimensions were determined and entered into a programmable calculator:

$l_o = 1.0013$ inches $t_o = 0.0358$ inches

Standard dimensions from the punch press die were entered:

$r_w = 0.2396$ inches $f_w = 0.2510$ inches

The specimen was strained to failure, yield was continuous and the maximum load was 378 lbs. The following dimensions were determined and entered into the calculator:

$l_f = 1.4782$ inches $t_f = 0.0340$ inches $fw_f = 0.2331$ inches

Calculations provided the following:

| | | |
|---|---|---|
| Ultimate Tensile Strength - from equation (2) | UTS | 42,278 psi |
| Percent Elongation from equation (3) | EL | 47.6% |
| Plastic Strain Ratio from equation (4) | r | 1.434 |
| Strain Hardening Exponent from equation (11) | n | 0.248 |
| Continuous Yield Strength from equation (18) using a constant of 0.02. | YSc | 22,628 psi |

The elapsed time to punch the specimen from a sample, measure, strain to failure, measure, calculate and readout was approximately five minutes.

EXAMPLE 2

A specimen was punched out from a sample of rimmed rolled sheet steel. The following dimensions were determined and entered into a programmable calculator:

$l_o = 1.0013$ inches $t_o = 0.0373$ inches

Standard dimensions from the punch press die were entered:

$r_w = 0.2936$ inches $f_w = 0.2510$ inches

The specimen was strained to failure providing a discontinuous yield load of 356 pounds and a maximum load of 421 pounds. The following dimensions were determined and entered into a calculator:

$l_f = 1.3758$ inches $t_f = 0.0355$ inches $fw_f = 0.2400$ inches

Calculations provided the following:

| | | |
|---|---|---|
| Ultimate Tensile Strength from equation (2) | UTS | 45,242 psi |
| Percent Elongation from equation (3) | EL | 37.4% |
| Plastic Strain Ratio from equation (4) | r | 0.906 |
| Strain Hardening Exponent from equation (11) | n | 0.202 |
| Discontinuous Yield Strength from equation (1) | YSd | 37,969 psi |

The elapsed time to punch the specimen from a sample, measure, strain to failure, measure, calculate and readout was just under five minutes.

The method just described provides a rapid method of determining the strain hardening exponent and other known useful properties of sheet metal without substantial skill or complex equipment. No particular testing speed is required, the determination of the strain hardening exponent by the described method is accurate within the range of conventional tensile testing times. The method applies to sheet metals other than steel such as copper, aluminum or titanium.

I claim:

1. A method for tensile testing a sheet metal specimen comprising the steps of preparing the specimen to have a reduced width portion for a part of the specimen length to be tested, thereby defining a full width section and a reduced width section, measuring the widths of the reduced width section and the full width section and the thickness of the specimen, straining the specimen to failure, measuring the thickness and width of the full width section, and calculating the strain hardening exponent of the sheet metal from the thickness and width measurements.

2. A method according to claim 1 in which the strain hardening exponent is calculated using the expression $$n = \frac{\ln rw + \ln t_o - \ln fw_f - \ln t_f - n}{\ln[\frac{(\ln fw_o + \ln t_o - \ln fw_f - \ln t_f)}{n}]}$$

where $\ln$ is the symbol for natural logarithms.

$n$ is the strain hardening exponent, $rw$ is the width of the reduced width section, $fw_o$ is the width of the full width section before straining to failure,
$t_o$ is the thickness before straining to failure,
$fw_f$ is the width of the full width section after straining to failure, and
$t_f$ is the thickness of the full width section after straining to failure.

3. A method according to claim 2 in which the specimen is prepared with the reduced width between 92% and 98% of the full width.

4. A method according to claim 3 in which the specimen is prepared with the reduced width between about 94.5% and about 95.5% of the full width.

5. A method according to claim 4 in which the specimen is punched out of the sheet metal.

6. A method according to claim 5 which includes the steps of
measuring the yield load while the specimen is being strained to failure,
calculating the yield strength from measurements of thickness, width and yield load, and
compensating the calculated yield strength for the effect of the sheared edges of the specimen.

7. A method according to claim 5 which includes the steps of
measuring the maximum load while the specimen is strained to failure,
calculating the ultimate tensile strength from measurements of thickness, width and maximum load, and
compensating the calculated ultimate tensile strength for the effect of the sheared edges of the specimen.

8. A method according to claim 7 which includes calculating the yield strength according to the expression $$YS = UTS\,(C/n)^n$$

where
$YS$ is the yield strength,
$UTS$ is the calculated and compensated ultimate strength,
$n$ is the calculated strain hardening exponent, and
$C$ is a constant.

9. A method according to claim 3 which includes the steps of
measuring the maximum load while the specimen is strained to failure,
calculating the ultimate strength from measurements of thickness, width and maximum load, and
calculating the yield strength according to the expression $$YS = UTS\,(C/n)^n$$

where
$YS$ is the yield strength,
$UTS$ is the calculated ultimate strength,
$n$ is the calculated strain hardening exponent, and
$C$ is a constant.

10. A method according to claim 1 in which the specimen is prepared with the reduced width between 92% and 98% of the full width.

11. A method according to claim 10 in which the specimen is prepared with the reduced width between about 94.5% and about 95.5% of the full width.

12. A method according to claim 11 in which the specimen is punched out of the sheet metal.

13. A method according to claim 12 which includes the steps of
measuring the yield load while the specimen is being strained to failure,
calculating the yield strength from measurements of thickness, width and yield load, and
compensating the calculated yield strength for the effect of the sheared edges of the specimen.

14. A method according to claim 12 which includes the steps of
measuring the maximum load while the specimen is strained to failure,
calculating the ultimate tensile strength from measurements of thickness, width and maximum load, and
compensating the calculated ultimate tensile strength for the effect of the sheared edges of the specimen.

15. A method according to claim 14 which includes calculating the yield strength according to the expression $$YS = UTS\,(C/n)^n$$

where
$YS$ is the yield strength,
$UTS$ is the calculated and compensated ultimate strength,
$n$ is the calculated strain hardening exponent, and
$C$ is a constant.

16. A method according to claim 10 which includes the steps of
measuring the maximum load while the specimen is strained to failure,
calculating the ultimate strength from measurements of thickness, width and maximum load, and
calculating the yield strength according to the expression $$YS = UTS\,(C/n)^n$$

where
$YS$ is the yield strength,
$UTS$ is the calculated ultimated strength,
$n$ is the calculated strain hardening exponent, and
$C$ is a constant.

* * * * *